United States Patent [19]

Kuwada et al.

[11] 4,002,638
[45] Jan. 11, 1977

[54] BENZAZEPINE DERIVATIVES

[75] Inventors: Yutaka Kuwada, Ashiya; Hiroyuki Tawada, Osaka; Kanji Meguro, Takarazuka, all of Japan

[73] Assignee: Takeda Chemical Industries, Ltd., Osaka, Japan

[22] Filed: Sept. 11, 1974

[21] Appl. No.: 505,088

[30] Foreign Application Priority Data

Sept. 14, 1973 Japan .............................. 48-104256
Feb. 26, 1974 Japan .............................. 49-023062
Jan. 10, 1974 Japan .............................. 49-006173

[52] U.S. Cl. .................. 260/308 C; 260/247.1 M; 260/247.2 R; 260/268 TR; 260/293.54; 424/269

[51] Int. Cl.² ...................................... C07D 249/12

[58] Field of Search ........................ 260/308 C

[56] References Cited
UNITED STATES PATENTS

| | | | |
|---|---|---|---|
| 3,853,882 | 12/1974 | Szmuszkovicz | 260/308 C |
| 3,876,634 | 4/1975 | Meguro et al. | 260/308 A |

*Primary Examiner*—Paul M. Coughlan, Jr.
*Attorney, Agent, or Firm*—Wenderoth, Lind & Ponack

[57] ABSTRACT

Novel benzazepine derivatives of the formula

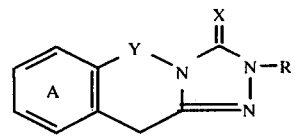

wherein ring A is unsubstituted or substituted by halogen, nitro, alkyl, alkoxy or trifluoromethyl, R is hydrogen or alkyl which may be substituted, X is oxygen or sulfur and Y is -$CH_2$-$CH_2$- or -CH=CH-, and their pharmaceutically acceptable salts, exhibit excellent pharmacological activities such as analgetic and muscle relaxing activities.

32 Claims, No Drawings

BENZAZEPINE DERIVATIVES

The present invention relates to novel and useful benzazepine derivatives.

The present inventors have succeeded in producing novel benzazepine derivatives of the formula

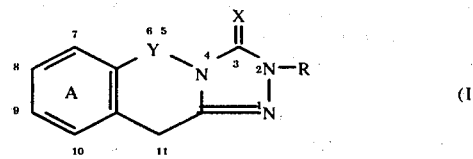

wherein ring A is unsubstituted or substituted by halogen, nitro, alkyl, alkoxy or trifluoromethyl, R is hydrogen or alkyl which may be substituted, X is oxygen or sulfur and Y is -CH$_2$-CH$_2$- or -CH=CH-, or their pharmaceutically acceptable salts, and further studies on these compounds have unexpectedly revealed that they exhibit excellent pharmacological activities such as analgetic and muscle relaxing activities.

Thus, the principle object of the present invention is to provide the novel benzazepine derivatives (I) as well as their salts which have the excellent pharmacological activities and another object is to provide a pharmaceutical composition comprising one or more of these compounds. A further object is to provide methods for the production of these novel and useful compounds. Other objects will be made clear from the description and claims hereinafter.

Referring to the formula (I), ring A is unsubstituted or substituted by one or more substituents at its optional position or positions. The halogen substituted on ring A includes chlorine, bromine, iodine and fluorine. The alkyl substituted on ring A is preferably one having 1 to 4 carbon atoms, such as methyl, ethyl, propyl, isopropyl, butyl, isobutyl, sec.-butyl, and tert.-butyl. The alkoxy substituted on ring A is preferably one having 1 to 4 carbon atoms, such as methoxy, ethoxy, propoxy, isopropoxy, butoxy, isobutoxy, sec.-butoxy, and tert.-butoxy.

As the alkyl designated by R in the formula (I), there may be mentioned, among others, straight-chained, branched or cyclic alkyl of about 1 to 6 carbon atoms, lower alkyl of about 1 to 3 carbon atoms being particularly desirable. Typical examples of the alkyl are methyl, ethyl, propyl, isopropyl, butyl, isobutyl, sec.-butyl, tert.-butyl, pentyl, hexyl, cyclopentyl, cyclohexyl, etc. When such an alkyl is further substituted, the substituent or substituents may be exemplified by hydroxy, lower alkoxy (e.g. methoxy, ethoxy, propoxy, isopropoxy, butoxy, isobutoxy, sec.-butoxy, tert.-butoxy, etc.), mono- or di-alkylamino (e.g. dimethylamino, methylamino, diethylamino, ethylamino, dipropylamino, propylamino, isopropylamino, etc.), mercapto, mercapto substituted by alkyl (e.g. methyl, ethyl, propyl, isopropyl, butyl, isobutyl, sec.-butyl, tert.-butyl, etc.), aryl which may be substituted by halogen (e.g. chlorine, bromine, iodine, and fluorine) or/and lower alkoxy (e.g. methoxy, ethoxy, propoxy, isopropoxy, butoxy, isobutoxy, sec.-butoxy, tert.-butoxy, etc.), cycloalkyl (e.g. cyclopropyl, cyclopentyl, cyclohexyl, etc.) and five-to six-membered heterocycle containing 1 or 2 hetero atoms such as nitrogen and/or oxygen (e.g. 1-pyrrolidinyl, morpholino, piperidino, piperazinyl, 4-substituted piperazinyl, etc.). An optional number of such substituents may be present in optional positions of the alkyl R.

The alkyl R having such substituents may be exemplified by cyclohexylmethyl, hydroxyethyl, hydroxypropyl, methoxyethyl, ethoxyethyl, dimethoxyethyl, diethoxyethyl, mercaptoethyl, methylmercaptoethyl, ethylmercaptoethyl, mercaptopropyl, methylmercaptopropyl, ethylmercaptopropyl, methylaminoethyl, dimethylaminoethyl, methylaminopropyl, dimethylaminopropyl, ethylaminoethyl, diethylaminoethyl, ethylaminopropyl, diethylaminopropyl, morpholinoethyl, (1-pyrrolidinyl)ethyl, morpholinopropyl, piperidinoethyl, piperazinylethyl, 4-methylpiperazinylethyl, 4-methylpiperizinylpropyl, 4-hydroxyethylpiperazinylethyl, 4-hydroxyethylpiperazinylpropyl, benzyl, phenethyl, p-chlorophenethyl, p-methoxyphenethyl, etc.

In the formula (I), when X is sulfur, it is preferable that R is hydrogen and Y is —CH=CH—.

The benzazepine derivatives (I) of the present invention can be produced, for example, by the following Processes A, B and/or C.

Process A

Among the benzazepine derivatives (I), compounds of the formula,

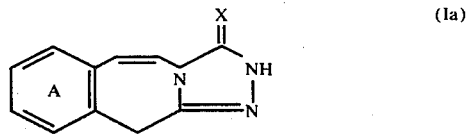

wherein ring A and X have the same meaning as hereinbefore defined, may be produced by cyclizing compounds of the formula

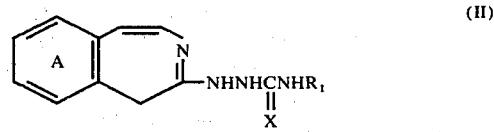

wherein ring A and X have the same meaning as hereinbefore defined and R$_1$ is a hydrocarbon residue.

Referring to the formula (II), as the hydrocarbon residue represented by R$_1$, there may be mentioned, among others, alkyl, aryl and aralkyl. The alkyl is preferably one having 1 to 4 carbon atoms, such as methyl, ethyl, propyl, isopropyl, butyl, isobutyl, sec.-butyl and tert.-butyl. The aryl is preferably phenyl, substituted phenyl such as lower alkyl substituted phenyl (e.g. tolyl, xylyl), halogen substituted phenyl (e.g. chlorophenyl) and naphthyl. The aralkyl is preferably one having up to about 8 carbon atoms, such as benzyl, and phenethyl.

The cyclization reaction of the compounds (II) can be easily achieved for example by heating the compounds (II) in the absence of a solvent up to around its melting point or by heating the compounds (II) in a suitable solvent up to around the boiling point of the solvent used. The temperature to be used for heating the compounds (II) in this cyclization varies with the melting point of the compounds (II) or the boiling point of a solvent used but it is ordinarily selected from within the range of about 50° C to 300° C. When a solvent is employed in this cyclization the solvent may be any solvent that does not interfere with the cyclization. Ordinarily preferred examples of said solvent are aromatic hydrocarbons (e.g. benzene, toluene, etc.), aromatic amines (e.g. pyridine), halogenated hydrocarbons (e.g. chloroform, and dichloromethane), ethers (e.g. diethyl ether, tetrahydrofuran, and dioxane), dimethylformamide, biphenyl, dimethylsulfoxide, etc.

Process B

Among the benzazepine derivatives (I), compounds of the formula

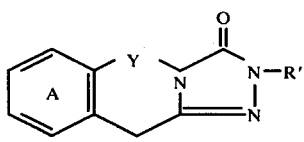
(Ib)

wherein ring A and Y have the same meaning as hereinbefore defined and R' is alkyl which may be substituted, may be produced by reacting benzazepine derivatives of the formula

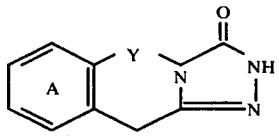
(Ic)

wherein ring A and Y have the same meaning as hereinbefore defined, with an alkylating agent capable of introducing the said R'.

Referring to the said benzazepine derivatives (Ic) employed in this process, those wherein Y is —CH=CH— may be produced by the above-mentioned Process A and those wherein Y is —CH$_2$—CH$_2$— may be produced by Process C mentioned hereinafter.

The alkyl shown by R' in the formula (Ib) means those mentioned in connection with R in the formula (I).

The alkylating agent to be employed in this alkylation process may be any reagent that is capable of introducing the alkyl R' on the nitrogen atom at 2-position of the compounds (Ic). Usually, preferred examples of said alkylating agent are dialkyl sulfates of the formula (R')$_2$SO$_4$ wherein R' has the same meaning as hereinbefore defined, and alkyl halides of the formula

R'Z wherein R' has the same meaning as hereinbefore defined, and Z is halogen such as those mentioned in connection with said substituent on ring A.

In this alkylation, it is not necessary to use a solvent, if the alkylating agent is employed in excess. However, the reaction can usually be conducted in a suitable solvent, such as alcohols (e.g. methanol, ethanol, etc.), hydrocarbons (e.g. benzene, toluene, xylene, etc.), dimethylformamide, dimethylsulfoxide, etc. In conducting the alkylation, a more desirable result in generally obtained when the nitrogen atom at 2-position of the compounds (Ic) is first converted to an alkali metal salt and, then the contemplated alkylation is performed. Such an alkali metal salt can be formed by using suitable alkali metal hydroxides (e.g. sodium hydroxide, potassium hydroxide, etc.) alkali metal alkoxides (e.g. sodium methoxide, potassium methoxide, sodium ethoxide, potassium ethoxide, potassium tert.-butoxide, etc.), alkali metal amides (e.g. sodium amide, potassium amide, etc.) and alkali metal hydrides (e.g. sodium hydride, lithium hydride, etc.). Generally, the portion of such a salt-forming reagent is desirably about 1 to 5 moles per mole of the compounds (Ic). The desirable proportion of the alkylating agent is ordinarily about 1 to 5 moles to each mole of the compounds (Ic).

While, usually, this reaction proceeds at and below room temperature, it may be carried out at elevated temperatures if necessary, so as to accelerate the reaction.

Process C

The benzazepine derivatives of the formula

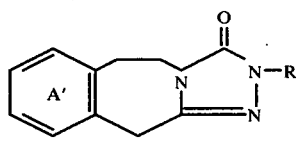
(Id)

wherein ring A' is unsubstituted or substituted by halogen, alkyl, alkoxy or trifluoromethyl and R has the same meaning as hereinbefore defined may be produced by reducing the compound of the formula

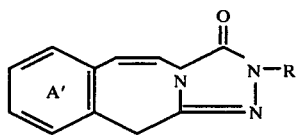
(Ie)

wherein ring A' and R have the same meaning as hereinbefore defined.

The benzazepine derivatives (Ie) employed in this process fall within the above-mentioned formula (Ib) or (Ic).

The reduction may be carried out by any reduction procedure that is able to selectively reduce the C$_{(5)}$–C$_{(6)}$ double bond. Among such procedures are catalytic reduction and the reduction process involving the use of sodium amalgam. Catalytic reduction is preferred.

The catalyst to be employed for said catalytic reduction may be any type of catalyst that is able to selectively reduce the C$_{(5)}$–C$_{(6)}$ double bond, and is exemplified by palladium, rhodium, nickel, etc. From practical points of view, palladium catalysts (e.g. palladium black, palladium-on-carbon, etc.) are particularly advantageous. Ordinarily this reaction is carried out in the presence of a solvent. Preferred examples of the solvent include alcohols (e.g. methanol, ethanol, propanol, etc.) and fatty acids and their esters (e.g. acetic acid, methyl acetate, ethyl acetate, etc.). To let the reaction proceed more readily and satisfactorily, there may be added to the reaction system an organic acid (e.g. acetic acid) or an inorganic acid (e.g. hydrochloric acid, sulfuric acid, etc.) if necessary. While this reaction usually proceeds at atmospheric temperature and pressure, it may be conducted, to accelerate the reaction, under adequate heating (near or over the boiling point of the solvent employed) and/or at elevated pressure.

The benzazepine derivatives (I), thus produced can be isolated in an optional purity by separation and purification procedures which are known per se, e.g. concentration, extraction chromatography, recrystallization, etc.

Since the benzazepine derivatives (I) contain a basic nitrogen atom in the molecule, they yield acid addition salts upon addition of an acid.

As said acid, there may be mentioned mineral acids (e.g. hydrochloric acid, hydrobromic acid, sulfuric acid, phosphoric acid, etc.), organic acids (e.g. acetic acid, oxalic acid, tartaric acid, p-toluenesulfonic acid, methanesulfonic acid, ethanesulfonic acid, etc.) and so on.

The benzazepine derivatives (I) and their salts have analgetic activity, muscle relaxing activity, etc., and are of value as medicines such as analgesics, muscle relaxants and so on. When the benzazepine derivatives (I) or their pharmaceutically acceptable salts are used as an analgesic, the benzazepine derivatives (I) or their pharmceutically acceptable salts can be orally or parenterally administered to mammals including human beings, either alone or in admixture with a pharmaceutically acceptable inert vehicle(s), in such suitable pharmaceutical forms as powders, granules, tablets, capsules, injections, suppositories, etc.

Pharmaceutical compositions containing one or more of the benzazepine derivatives (I) or their salts can be prepared by conventional methods for the preparation of powders, granules, tablets, capsules, injections, suppositories and the like. The choice of carriers may be determined depending upon the route of administration, the solubility of benzazepine derivatives (I) and their salts, and so on.

While the dosage of the benzazepine derivatives (I) or their salts depends upon the particular species of compound or salt, the symptoms to be dealt with, the seriousness of illness, etc., the daily oral dosage is ordinarily about 10 mg. to 250 mg. per adult human.

Some examples of practical recipes in which the benzazepine derivatives of this invention can be utilized as analgesics are as follows.

| Tablet: | |
|---|---|
| 2,11-dihydro-2-methyl-3H-s-triazolo-[3,4-b][3]benzazepine-3-one | 5 mg. |
| lactose | 60 mg. |
| corn starch | 33.5 mg. |
| gelatin | 1 mg. |
| magnesium stearate | 0.5 mg. |
| | 100 mg. per tablet |

| Tablet: | |
|---|---|
| 2,11-dihydro-3H-s-triazolo[3,4-b][3]-benzazepine-3-one | 10 mg. |
| lactose | 60 mg. |
| corn starch | 28.5 mg. |
| gelatin | 1 mg. |
| magnesium stearate | 0.55 mg. |
| | 100 mg. per tablet |

The typical examples of the benzazepine derivatives (I) are shown below. The indications of A, B and/or C in the brackets after the respective names of the compounds show the foregoing Process A, B and/or C by which the respective compounds may be produced.

2,11-Dihydro-3H-s-triazolo[3,4-b][3]benzazepin-3-one [A]

2,11-Dihydro-3H-s-triazolo[3,4-b][3]benzazepine-3-thione [A]

2,11-Dihydro-8,9-dimethoxy-3H-s-triazolo[3,4-b][3]benzazepine-3-thione [A]

7-Chloro-2,11-dihydro-3H-s-triazolo[3,4-b][3]benzazepin-3-one [A]

2,11-Dihydro-8,9-dimethoxy-3H-s-triazolo[3,4-b][3]benzazepin-3-one [A]

7-Chloro-2,11-dihydro-3H-s-triazolo[3,4-b][3]benzazepine-3-thione [A]

10-Chloro-2,11-dihydro-3H-s-triazolo[3,4-b][3]benzazepin-3-one [A]

10-Chloro-2,11-dihydro-3H-s-triazolo[3,4-b][3]benzazepine-3-thione [A]

2,11-Dihydro-8,9-dimethyl-3H-s-triazolo[3,4-b]B][3]benzazepin-3-one [A]

2,11-Dihydro-8,9-dimethyl-3H-s-triazolo[3,4-b][3]benzazepine-3-thione [A]

2-Ethyl-2,11dihydro-3H-s-triazolo[3,4-b][3]benzazepin-3-one [B]

2,5,6,11-Tetrahydro-2-methyl-3H-s-triazolo[3,4-b][3]benzazepin-3-one [B or C]

10-Chloro-2,11-dihydro-2-methyl-3H-s-triazolo[3,4-b][3]benzazepin-3-one [B]

2,11-Dihydro-2,8,9-trimethyl-3H-s-triazolo[3,4-b][3]benzazepin-3-one [B]

2-(2-Dimethylaminoethyl)-2,11-dihydro-3H-s-triazolo[3,4-b][3]benzazepin-3-one [B]

2,11-Dihydro-8,9-dimethyoxy-2-methyl-3H-s-triazolo[3,4-b][3]benzazepin-3-one [B]

2-Ethyl-2,5,6,11-tetrahydro-3H-s-triazolo[3,4-b][3]benzapezin-3-one [B or C]

2,11-Dihydro-2-propyl-3H-s-triazolo[3,4-b][3]benzazepin-3-one [B]

2,11-Dihydro-2-isopropyl-3H-s-triazolo[3,4-b][3]benzazepin-3-one [B]

2-Butyl-2,11-dihydro-3H-s-triazolo[3,4,-b][3]benzazepin-3-one [B]

2,11-Dihydro-2-hexyl-3H-s-triazolo[3,4-b][3]benzazepin-3-one [B]

2-Cyclohexyl-2,11-dihydro-3H-s-triazolo[3,4-b][3]benzazepin-3-one [B]

2,11-Dihydro-2-phenethyl-3H-s-triazolo[3,4-b][3]benzazepin-3-one [B]

2-Cyclopropylmethyl-2,11-dihydro-3H-s-triazolo[3,4-b][3]benzazepin-3-one [B]

2-(3-Dimethylaminoethyl)-2,11-dihydro-3H-s-triazolo[3,4-b][3]benzazepin-3-one [B]

2-(3-Diethylaminoethyl)-2,11-dihydro-3H-s-triazolo[3,4-b][3]benzazepin-3-one [B]

2-(3-Dimethylaminopropyl)-2,11-dihydro-3H-s-triazolo[3,4-b][3]benzazepin-3-one [B]

2,11-Dihydro-2-morpholinoethyl-3H-s-triazolo[3,4-b][3]benzazepin-3-one [B]

2,11-Dihydro-2-piperidinoethyl-3H-s-triazolo[3,4-b][3]benzazepin-3-one [B]

2,11-Dihydro-2-piperidinoethyl-3H-s-triazolo[3,4-b][3]benzazepin-3-one [B]

2,11-dihydro-2-(4-methylpiperazinoethyl)-3H-s-triazolo[3,4-b][3]benzazepin-3-one [B]

2,11-Dihydro-2-[4-(2-hydroxyethyl)piperazinoethyl]-3H-s-triazolo[3,4-b][3]benzazepin-3-one [B]

2,11-Dihydro-2-(2-hydroxyethyl)-3H-s-triazolo[3,4-b][3]benzazepin-3-one [B]

2,11-Dihydro-2-(2-methoxyethyl)-3H-s-triazolo[3,4-b][3]benzazepin-3-one [B] 2-(3-Bromopropyl)-

2,11-dihydro-3H-s-triazolo[3,4-b][3]-benzazepin-3-one [B]
2-(2-Ethylmercaptoethyl)-2,11-dihydro-3H-s-triazolo[3,4-b][3]benzazepin-3-one [B]
2,5,6,11-Tetrahydro-2-propyl-3H-s-triazolo[3,4-b][3]benzazepin-3-one [B or C]
2-Benzyl-2,5,6,11-tetrahydro-3H-s-triazolo[3,4-b][3]-benzazepin-3-one [B or C]
2-(2-Dimethylaminoethyl)-2,5,6,11-tetrahydro-3H-s-triazolo[3,4-b][3]benzazepin-3-one [B or C]
2,5,6,11-Tetrahydro-2-(2-methoxyethyl)-3H-s-triazolo[3,4-b][3]benzazepin-3-one [B or C]
7-Chloro-2,11-dihydro-2-methyl-3H-s-triazolo[3,4-b][3]-benzazepin-3-one [B]
8-Chloro-2,11-dihydro-2-methyl-3H-s-triazolo[3,4-b][3]benzazepin-3-one [B]
9-Chloro-2,11-dihydro-2-methyl-3H-s-triazolo[3,4-b][3]benzazepin-3-one [B]
7-Chloro-2-ethyl-2,11-dihydro-3H-s-triazolo[3,4-b][3]benzazepin-3-one [B]
10-Chloro-2ethyl-2,11-dihydro-3H-s-triazolo[3,4-b][3]benzazepin-3-one [B]
2-butyl-7-chloro-2,11-dihydro-3H-s-triazolo[3,4-b][3]benzazepin-3-one [B]
2-Benzyl-10-chloro-2,11-dihydro-3H-s-triazolo[3,4-b][3]benzazepin-3-one [B]
10-chloro-2-(2-dimethylaminoethyl)-2,11-dihydro-3H-s-triazolo[3,4-b][3]benzazepin-3-one [B]
10-chloro-2,11-dihydro-2-(2-methoxyethyl)-3H-s-triazolo[3,4-b][3]benzazepin-3-one [B]
7-Chloro-2,5,6,11-tetrahydro-2-methyl-3H-s-triazolo[3,4-b][3]benzazepin-3-one [B or C]
10-Chloro-2,5,6,11-tetrahydro-2-methyl-3H-s-triazolo[3,4-b][3]benzazepin-3-one [B or C]
7Chloro-2-ethyl-2,5,6,11-tetrahydro-3H-s-triazolo[3,4-b][3]benzazepin-3-one [B or C]
10-Chloro-2-ethyl-2,5,6,11-tetrahydro-3H-s-triazolo[3,4-b][3 ]benzazepin-3-one [B or C]
2-butyl-7-chloro-2,5,6,11-tetrahydro-3H-s-triazolo[3,4-b][3]benzazepin-3-one [B or C]
10-Chloro-2-hexyl-2,5,6,11-tetrahydro-3H-s-triazolo[3,4-b][3]benzazepin-3-one [B or C]
2-Benzyl-10-chloro-2,5,6,11-tetrahydro-3H-s-triazolo [3,4-b][3]benzazepin-3-one [B or C]
10-Chloro-2-(2-dimethylaminoethyl)-2,5,611-tetrahydro-3H-s-triazolo[3,4-b][3]benzazepin-3-one [B or C]
10-Chloro-2,5,6,11-tetrahydro-2-(2-methoxyethyl)-3H-s-triazolo[3,4-b][3]benzazepin-3-one [B or C]
2-Ethyl-2,11-dihydro-8,9-dimethoxy-3H-s-triazolo[3,4-b][3]benzazepin-3-one [B]
2-Butyl-2,11-dihydro-8,9-dimethoxy-3H-s-triazolo[3,4-b][3]benzazepin-3-one [B]
2-Benzyl-2,11-dihydro-8,9-dimethoxy-3H-s-triazolo[3,4-b][3]benzazepin-3-one [B]
2-cyclopropylmethyl-2,11-dihydro-8,9-dimethoxy-3H-s-triazolo[3,4-b][3]benzazepin-3-one [B]
2-(2-dimethylaminoethyl)-2,11-dihydro-8,9-dimethoxy-3H-s-triazolo[3,4-b][3]benzazepin-3-one [B]
2,11-Dihydro-8,9-dimethoxy-2-(2-methoxyethyl)-3H-s-triazolo[3,4-b][3]benzazepin-3-one [B]
2,5,6,11-tetrahydro-8,9-dimethoxy-22-—methyl-3H-s-triazolo[3,4-b][3]benzazepin-3-one [B or C]
2-Ethyl-2,5,6,11-tetrahydro-8,9-dimethoxy-3H-s-triazolo[3,4-b][3]benzazepin-3-one [B or C]

2-Ethyl-2,11-dihydro-8,9-dimethyl-3H-s-triazolo[3,4-b][3]benzazepin-3-one [B]
2-Butyl-2,11-dihydro-8,9-dimethyl-3H-s-triazolo[3,4-b][3]benzazepin-3-one [B]
2-Benzyl-2,11-dihydro-8,9-dimethyl-3H-s-triazolo[3,4-b][3]benzazepin-3-one [B]
2-Cyclopropylmethyl-2,11-dihydro-8,9-dimethyl-3H-s-triazolo[3,4-b][3]benzazepin-3-one [B]
2-(2-Dimethylaminoethyl)-2,11-dihydro-8,9-dimethyl-3H-s-triazolo[3,4-b][3]benzazepin-3-one [B]
2,11-Dihydro-2-(2-methoxyethyl)-8,9-dimethyl-3H-s-triazolo[3,4-b][3]benzazepin-3-one [B]
2,5,6,11-Tetrahydro-2,8,9-trimethyl-3H-s-triazolo[3,4-b][3]benzazepin-3-one [B or C]
2-Ethyl-2,5,6,11-tetrahydro-8,9-dimethyl-3H-s-triazolo[3,4-b][3]benzazepin-3-one [B or C]
2-Butyl-2,5,6,11-tetrahydro-8,9-dimethyl-3H-s-triazolo[3,4-b][3]benzazepin-3-one [B or C]
2,5,6,11-tetrahydro-8,9-dimethyl-2-(2-dimethylaminoethyl)-3H-s-triazolo[3,4-b][3]benzazepin-3-one [B or C]
2,5,6,11-Tetrahydro-8,9-dimethyl-3H-s-triazolo[3,4-b][3]benzazepin-3-one [C]
2,5,6,11-Tetrahydro-8,9-dimethoxy-3H-s-triazolo[3,4-b][3]benzazepin-3-one [C]
2-Hexyl-2,5,6,11-tetrahydro-3H-s-triazolo[3,4-b][3]benzazepin-3-one [B or C]
2-Benzyl-2,5,6,11-tetrahydro-3H-s-triazolo[3,4-b][3]benzazepin-3-one [B or C]
2,5,6,11-Tetrahydro-3H-s-triazolo[3,4-b][3]benzazepin-3-one [C]
2-Cyclopropylmethyl-2,5,6,11-tetrahydro-3H-s-triazolo[3,4-b][3]benzazepin-3-one [B or C]
2-(3-Diethylaminoethyl)-2,5,6,11-tetrahydro-3H-s-triazolo[3,4-b][3]benzazepin-3-one [B or C]
2-(3-Dimethylaminopropyl)-2,5,6,11-tetrahydro-3H-s-triazolo[3,4-b][3]benzazepin-3-one [B or C]
2,5,6,11-Tetrahydro-2-(2-morpholinoethyl)-3H-s-triazolo[3,4-b][3]benzazepin-3-one [B or C]
2,5,6,11-Tetrahydro-2-(2-piperidinoethyl)-3H-s-triazolo[3,4-b][3]benzazepin-3-one [B or C]
2,5,6,11-Tetrahydro-2-(2-piperazinylethyl)-3H-s-triazolo[3,4-b][3]benzazepin-3-one [B or C]
2,5,6,11-Tetrahydro-2-[2-(4-methylpiperazinyl)ethyl]-3H-s-triazolo[3,4-b][3]benzazepin-3-one [B or C]
2,5,6,11-Tetrahydro-2- 2-[4-(2-hydroxyethyl)-piperazinyl]ethyl -3H-s-triazolo[3,4-b][3]benzazapin-3-one [B or C]
2,5,6,11-Tetrahydro-2-(2-hydroxyethyl)-3H-s-triazolo[3,4-b][3]benzazepin-3-one [B or C]
2-(2-Ethylmercaptoethyl)-2,5,6,11-tetrahydro-3H-s-triazolo[3,4-b][3]benzazepin-3-one [B or C]
7-Chloro-2,5,6,11-tetrahydro-3H-s-triazolo[3,4-b][3]benzazepin-3-one [C]
8-Chloro-2,5,6,11-tetrahydro-3H-s-triazolo[3,4-b][3]benzazepin-3-one [C]
8-Chloro-2,5,6,11-tetrahydro-2-methyl-3H-s-triazolo[3,4-b][3]benzazepin-3-one [B or C]
9-Chloro-2,5,6,11-tetrahydro-3H-s-triazolo[3,4-b][3]benzazepin-3-one [C]
9-Chloro-2,5,6,11-tetrahydro-2-methyl-3H-s-triazolo[3,4-b][3]benzazepin-3-one [B or C]
10-Chloro-2,5,6,11-tetrahydro-3H-s-triazolo[3,4-b][3]benzazepin-3-one [C]
2,5,6,11-Tetrahydro-8,9-dimethoxy-3H-s-triazolo[3,4-b][3]benzazepin-3-one [C]

2,5,6,11-Tetrahydro-8,9-dimethyl-3H-s-triazolo[3,4-b][3]benzazepin-3-one [C]

The starting compounds (II) can be produced, for example, by the following procedure:

The compounds (IV) thus produced can be recovered in optional purity by separation and purification procedures which are known per se, such as concentration, extraction, chromatography, recrystallization, etc.

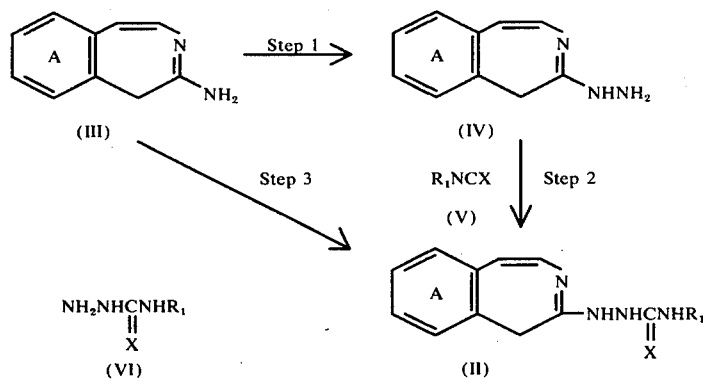

wherein ring A, X and $R_1$ have the same meaning as hereinbefore defined.

Steps 1 to 3 are particularly mentioned below:

The compounds (III) can be produced, for example, by the procedure described in Journal of Heterocyclic Chemistry, 2, 26(1965) or by the following procedure which is analogous thereto.

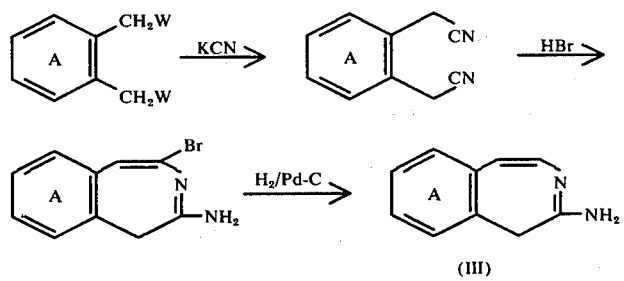

Step 1

Step 1 consists in reacting the compounds (III) with hydrazine. Hydrazine is ordinarily used in the form of hydrazine hydrate, the amount of which is ordinarily about 1 to 5 moles per mole of the compounds (III). Ordinarily the reaction of this step is preferably conducted in a solvent such as alcohols (e.g. methanol, ethanol, propanol, isopropanol, butanol, etc.), although other solvents can also be employed insofar as they do not interfere with the contemplated reaction. Typical examples of such other solvents are benzene, toluene, chloroform, dichloromethane, dimethylformamide, etc. The reaction temperature of this step is selected from within the range of about $-10°$ C to $100°$ C but, ordinarily, the reaction proceeds satisfactorily at around room temperature. Further, the reaction of this step proceeds more advantageously in the presence of an acid catalyst. As the acid catalyst, there may be mentioned organic acids such as lower aliphatic carboxylic acids (e.g. acetic acid, propionic acid, etc.), organic sulfonic acids (e.g. p-toluenesulfonic acid, methanesulfonic acid, ethanesulfonic acid, etc.) and mineral acids (e.g. hydrochloric acid, hydrobromic acid, sulfuric acid, etc.).

In using such an acid catalyst in the reaction, the acid may be added to the reaction system or, alternatively, it may be added in the form of acid addition salt with the compounds (III) or hydrazine. Ordinarily the amount of said acid catalyst is about 1 to 2 moles per mole of the compounds (III).

wherein W is halogen, and ring A has the same meaning as hereinbefore defined.

Step 2

Step 2 consists in reacting the compounds (IV) with the compounds (V).

The amount of such compounds (V) is ordinarily about 1 to 2 moles per mole of the compounds (IV). The reaction of this step is carried out ordinarily in a suitable solvent. The solvent just mentioned may be any solvent that does not interfere with the contemplated reaction. Ordinarily preferred examples of said solvent are aromatic hydrocarbons (e.g. benzene, toluene, etc.), aromatic amines (e.g. pyridine), halogenated hydrocarbons (e.g. chloroform, and dichloromethane), ethers (e.g. diethyl ether, tetrahydrofuran, and dioxane), dimethylformamide, etc. The reaction temperature of this step is ordinarily selected from within the range of about $-10°$ C to about $50°$ C.

Step 3

Step 3 consists in reacting the compounds (III) with the compounds (VI).

In this case, the amount of the compounds (VI) is ordinarily about 1 to 5 moles per mole of the compounds (III), and the reaction can be carried out, with or without a solvent, in the presence of an acid catalyst which is similar to those used in step 1.

The reaction temperature is ordinarily selected from within the range of about $-10°$ C to about $100°$ C.

The compounds (II) thus produced can be isolated and purified to an optional purity by separation and purification procedures which are known per se, such as concentration, extraction, chromatography, recrystallization, etc. This isolation and purification is not always essential. The reaction mixture obtained may be subjected, as it is, to the cylization reaction mentioned as Process A.

The following Reference Examples and Examples are further illustrative of this invention. It should, of course, be understood that the scope of the invention is by no means limited by and to these examples.

Throughout the foregoing description as well as in the following Reference Examples, Examples and Claims, "° C", "n" and "mg.", respectively denote "degrees centigrade", "normal(s)" and "milligram(s)". The word "part(s)" is based on weight unless otherwise noted and the relationship between "part(s)" and "volume part(s)" corresponds to that between "gram(s)" and "milliliter(s)".

REFERENCE EXAMPLE 1

To a solution of 9,.55 parts of 2-amino-1H-3-benzazepine hydrobromide in 120 volume parts of methanol is added dropwise 8.1 volume parts of hydrazine hydrate (100%) under stirring. After stirring for 15 minutes, the mixture is added to water and extracted with chloroform.

The chloroform layer is washed with water and dried over sodium sulfate. After evaporation of the solvent, the crystalline residue is collected by filtration, washed with n-hexane and dried, whereupon 2-hydrazino-1H-3-benzazepine is obtained as crystals. Recrystallization from chloroform gives colorless needles melting at 148° – 151° C.

Elemental analysis, $C_{10}H_{11}N_2$: Calculated C, 69.34; H, 6.40; N, 24.26; Found C, 68.99; H, 6.42; N, 24.56.

By a procedure similar to that described in the above Reference Example 1, the following compounds can be prepared.

2-Hydrazino-7,8-dimethoxy-1H-3-benzazepine, colorless needles (recrystallized from chloroform-ether), m.p. 165° – 168° C (softening), 212° – 215° C.
6-Chloro-2-hydrazino-1H-3-benzazepine.
9-Chloro-2-hydrazino-1H-3-benzazepine.
7,8-Dimethyl-2-hydrazino-1H-3-benzazepine.

REFERENCE EXAMPLE 2

To a solution of 1.7 parts of 2-hydrazino-1H-3-benzazepine in 30 volume parts of pyridine is added 0.6 volume part of methyl isocyanate under ice-cooling and stirring. After stirring for 20 minutes, the mixture is added to a mixture of 100 volume parts of water and 25 volume parts of acetic acid and extracted with chloroform. The chloroform layer is washed with water and dried over sodium sulfate.

The chloroform is distilled off and the residue is treated with diethyl ether, whereupon 2-(4-methylsemicarbazido)-1H-3-benzazepine is obtained as crystals. Recrystallization from methanol gives colorless meedles melting at 200° – 201° C.

Elemental analysis, $C_{12}H_{14}N_4O$: Calculated C, 62.59; H, 6.13; N, 24.33; Found C, 62.49; H, 5.78; N, 24.04.

The above reaction also proceeds smoothly when dichloromethane or tetrahydrofuran, instead of pyridine, is used as the solvent. By a procedure similar to that used in Reference Example 2, the following compounds are produced.

2-(4-Ethylsemicarbazido)-1H-3-benzazepine
2-(4-Phenylsemicarbazido)-1H-3-benzazepine
2-(4-Benzylsemicarbazido)-1H-3-benzazepine
2-(4-Methylthiosemicarbazido)-1H-3-benzazepine
2-(4-Phenylthiosemicarbazido)-1H-3-benzazepine
2-Chloro-2-(4-methylsemicarbazido)-1H-3-benzazepine
6-Chloro-2-(4-phenylthiosemicarbazido)-1H-3-benzazepine
9-Chloro-2-(4-methylsemicarbazido)-1H-3-benzazepine
9-Chloro-2-(4-phenylthiosemicarbazido)-1H-3-benzazepine
7,8-Dimethyl-2-(4-methylsemicarbazido)-1H-3-benzazepine
7,8-Dimethyl-2-(4-phenylthiosemicarbazido)-1H-3-benzazepine
7,8-Dimethoxy-2-(4-methylsemicarbazido)-1H-3-benzazepine
7,8-Dimethoxy-2-(4-phenylthiosemicarbazido)-1H-3-benzazepine

EXAMPLE 1

To a solution of 17.3 parts of 2-hydrazino-1H-3-benzazepine in 3 volume parts of dry pyridine is added dropwise 6 parts of methylisocyanate.

The mixture is allowed to stand at room temperature for 30 minutes, then 300 volume parts of dimethylformamide is added thereto. After refluxing the mixture for 6 hours, the solvent is distilled off under reduced pressure. The residue is treated with ethyl acetate to obtain 2,11-dihydro-3H-s-triazolo-[3,4-b][3]benzazepin-3-one as crystals. Recrystallization from methanol gives colorless needles melting at 209° – 210° C.

Elemental analysis, $C_{11}H_9N_3O$;
Calculated C, 66.32; H, 4.55; N, 21.10;
Found C, 66.21; H, 4.73; N, 20.74.

EXAMPLE 2

A solution of 46 parts of 2-(4-methylsemicarbazidol)-1H-3-benzazepine in a mixture of 600 volume parts of dimethylformamide and 600 volume parts of pyridine is refluxed for 7 hours and then the solvents are evaporated under reduced pressure. The residue is treated with diethyl ether to obtain 2,11-dihydro-3H-s-triazolo[3,4-b][3]benzazepin-3-one as crystals melting at 208° – 210° C.

This product is identical with the product prepared in Example 1.

EXAMPLE 3

Under cooling with ice and stirring, 12 volume parts of phenyl isothiocyanate is added dropwise to a solution of 17.3 parts of 2-hydrazinc-1H-3-benzazepine in 300 volume parts of dry pyridine. The mixture is stirred at room temperature for 30 minutes and then refluxed for 2 hours. After evaporation of the solvent under reduced pressure, the residue is treated with diethyl ether, whereupon 2,11-dihydro-3H-s-triazolo[3,4-b][3]benzazepine-3-thione is obtained as crystals. Recrystallization from chloroform-methanol gives colorless prisms melting at 231° C.

Elemental analysis, $C_{11}H_9N_2S$;
Calculated C, 61.37; H, 4.21; N, 19.52;
Found C, 61.33; H, 3.97; N, 19.36.

EXAMPLE 4

By a procedure similar to that described in the above Example 1, the following benzazepine derivatives can be produced.

2,11-Dihydro-8,9-dimethoxy-3H-s-triazolo[3,4-b][3]-benzazepin-3-one, colorless needles (recrystallized from chloroform-methanol), melting at 273° – 274° C.

EXAMPLE 5

To a solution of 8 parts of 2,11-dihydro-3H-s-triazolo-[3,4-b][3]benzazepin-3-one in 80 volume parts of dimethylformamide is added 9 volume parts of 5N aqueous sodium hydroxide solution and then 3 volume parts of methyl iodide is added dropwise under stirring. After stirring for 1 hour, the reaction mixture is diluted with water and extracted with ethyl acetate. The ethyl acetate layer is washed with water and the solvent is distilled off. The precipitate is collected by filtration to give 2,11-dihydro-2-methyl-3H-s-triazolo-[3,4-b][3]benzazepin-3-one as crystals. Recrystallization from isopropyl ether gives light-brown needles melting at 123° –124° C.

Elemental analysis, $C_{12}H_{11}N_3O$:
Calculated C, 67.59; H, 5.20; N, 19.71;
Found C, 67.79; H, 5.13; N, 19.63.

EXAMPLE 6

To a solution of 20 parts of 2,11-dihydro-3H-s-triazolo-[3,4-b][3]benzazepin-3-one in 300 volume parts of dimethylformamide is added 5.5 parts of a sodium hydride (55%) dispersion in mineral oil under stirring. To the mixture is added 13 volume parts of benzyl bromide dropwise. After stirring for 1 hour, the crystals are collected by filtration to give 2-benzyl-2,11-dihydro-3H-s-triazolo[3,4-b][3]benzazepin-3-one as crystals. Recrystallization from ethanol gives colorless plates melting at 133° – 134° C.

Elemental analysis, $C_{18}H_{15}N_3O$:
Calculated C, 74.72; H, 5.23; N, 14.53;
Found C, 74.99; H, 5.03; N, 14.57.

EXAMPLE 7

By a procedure similar to that described in the above Example 5 or 6, the following benzazepine derivatives can be produced.

2-Ethyl-2,11-dihydro-3H-s-triazolo[3,4-b][3]benzazepin-3-one, colorless needles (recrystallized from aqueous alcohol), melting at 125° – 126° C.

2,5,6,11-Tetrahydro-2-methyl-3H-s-triazolo[3,4-b][3]benzazepin-3-one, colorless prisms (recrystallized from ethanol), melting at 187° C.

10-Chloro-2,11-dihydro-2-methyl-3H-s-triazolo[3,4-b][3]benzazepin-3-one, colorless needles (recrystallized from methanol), melting at 199° – 200° C.

2,11-Dihydro-2,8,9-trimethyl-3H-s-triazolo[3,4-b][3]benzazepin-3-one, colorless needles (recrystallized from ethanol), melting at 160° – 161° C.

2-(2-Dimethylaminoethyl)-2,11-dihydro-3H-s-triazolo[3,4-b][3]benzazepin-3-one oxalate (recrystallized from methanol), melting at 205° – 207° C.

2,11-Dihydro-8,9-dimethoxy-2-methyl-3H-s-triazolo[3,4-b][3]benzazepin-3-one (recrystallized from chloroform-methanol), melting at 210° – 211° C.

2-Ethyl-2,5,6,11-tetrahydro-3H-s-triazolo[3,4-b][3]benzazepin-3-one, colorless prisms (recrystallized from aqueous ethanol), melting at 122° – 123° C.

EXAMPLE 8

A mixture of 20 parts of 2,11-dihydro-3H-s-triazolo[3,4-b][3]benzazepin-3-one, 400 volume parts of acetic acid and 15 parts of 5% palladium-on-carbon is hydrogenated at atmospheric pressure and temperature under stirring. After 2600 volume parts of hydrogen is absorbed, the catalyst is removed by filtration. The filtrate is concentrated under reduced pressure and the residue is treated with diethyl ether to give 2,5,6,11-tetrahydro-3H-s-triazolo[3,4-b][3]benzazepin-3-one as crystals. Recrystallization from ethanol gives colorless plates melting at 253° – 261° C.

Elemental analysis, $C_{11}H_{11}N_3O$:
Calculated C, 65.67; H, 5.51; N, 20.88;
Found C, 65.94; H, 5.08; N, 20.94.

EXAMPLE 9

In a manner similar to that described in Example 8, the following compounds are produced.

2,5,6,11-Tetrahydro-2-methyl-3H-s-triazolo[3,4-b][3]benzazepin-3-one, colorless prisms (recrystallized from ethanol), melting at 187° C.

2-Ethyl-2,5,6,11-tetrahydro-3H-s-triazolo[3,4-b][3]benzazepin-3-one, colorless prisms (recrystallized from aqueous ethanol), melting at 122° – 123° C.

2,5,6,11-Tetrahydro-8,9-dimethyl-3H-s-triazolo[3,4-b][3]benzazepin-3-one, colorless plates (recrystallized from chloroform-methanol), melting at 285° – 292° C.

2,5,6,11-Tetrahydro-8,9-dimethoxy-3H-s-triazolo[3,4-b][3]benzazepin-3-one, colorless needles (recrystallized from methanol), melting at 259° – 263° C.

EXAMPLE 10

A solution of 24 parts of 2-amino-1H-3-benzazepine hydrobromide, 33 parts of semicarbazide hydrochloride, and 40 parts of potassium acetate in 500 volume parts of methanol is stirred at room temperature overnight. After dilution with water the reaction mixture is neutralized with an aqueous solution of sodium bicarbonate and, then, extracted with chloroform. The chloroform layer is dried over sodium sulfate. Evaporation of the solvent gives 2-semicarbazido-1H-3-benzazepine as crystals. Recrystallization from methanol gives colorless prisms, melting at 188° – 189° C.

Elemental analysis, $C_{11}H_{12}N_4O$:
Calculated C, 61.09; H, 5.59; N, 25.91;
Found C, 60.81; H, 5.31; N, 25.82.

A mixture of 65 parts of the 2-semicarbazido-1H-3-benzazepine and 2000 volume parts of dimethylformamidepyridine (1:1) is refluxed for 1 hour. The solvent is evaporated and the residue is treated with ethanol-diethyl ether to give 2,11-dihydro-3H-s-triazolo[3,4-b][3]benzazepin-3-one as crystals, melting at 207° – 208° C. This product is identical with that obtained in Example 1.

EXAMPLE 11

In a manner similar to that described in Example 10, the following compounds can be produced.

2,11-dihydro-7,8-dimethyl-3H-s-triazolo[3,4-b][3]benzazepin-3-one, colorless needles (recrystallized from chloroform-methanol), melting at 265° – 269° C.

10-Chloro-2,11-dihydro-3H-s-triazolo[3,4-b][3]benzazepin-3-one, colorless needles (recrystallized from chloroformmethanol), melting at 290° – 295° C.

7-Chloro-2,11-dihydro-3H-s-triazolo[3,4-b][3]benzazepin-3-one, colorless needles (recrystallized from chloroform-methanol), melting at 280° – 287° C.

What is claimed is:

1. A compound selected from the group consisting of compounds of the formula

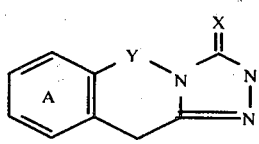

wherein ring A is unsubstituted or substituted by at least one of halogen, nitro, alkyl of 1–4 carbon atoms, alkoxy of 1–4 carbon atoms and trifluoromethyl,
R is hydrogen, alkyl of 1–6 carbon atoms, cyclopentyl or cyclohexyl, said alkyl, cyclopentyl and cyclohexyl groups designated by R being unsubstituted or substituted by at least one of (1) hydroxy, (2) alkoxy of 1–4 carbon atoms, (3) monoalkylamino of 1–3 carbon atoms, (4) dialkylamino of 1–3 carbon atoms in each alkyl group, (5) mercapto, (6) mercapto substituted by alkyl of 1–4 carbon atoms, (7) phenyl, (8) phenyl substituted by at least one of halogen and alkoxy of 1–4 carbon atoms, (9) cyclopropyl, (10) cyclopentyl, (11) cyclohexyl, (12) unsubstituted 1-pyrrolidinyl, (13) unsubstituted morpholino, (14) unsubstituted piperidino, (15) unsubstituted piperazinyl, (16) 4-methylpiperazinyl and (17) 4-hydroxyethylpiperazinyl,
X is oxygen or sulfur, and
Y is —CH$_2$—CH$_2$— or —CH=CH—,
and pharmaceutically acceptable salts thereof.

2. A compound according to claim 1, wherein X is oxygen.

3. A compound according to claim 1, wherein X is sulfur.

4. A compound according to claim 1, wherein Y is —CH=CH—.

5. A compound according to claim 1, wherein Y is —CH$_2$—CH$_2$—.

6. A compound according to claim 1, wherein R is hydrogen.

7. A compound according to claim 1, wherein ring A is substituted by halogen, nitro, alkyl of 1–4 carbon atoms, alkoxy of 1–4 carbon atoms or trifluoromethyl.

8. The compound according to claim 1, wherein ring A is unsubstituted.

9. A compound according to claim 1, wherein X is oxygen and R is alkyl of 1–6 carbon atoms which is unsubstituted or substituted as defined in claim 1.

10. A compound according to claim 1, wherein X is oxygen and Y is —CH=CH—.

11. A compound according to claim 1, wherein X is oxygen, Y is —CH=CH— and R is alkyl of 1–6 carbon atoms which is unsubstituted or substituted as defined in claim 1.

12. A compound according to claim 1, wherein R is alkyl of 1–6 carbon atoms which is unsubstituted or substituted as defined in claim 1.

13. A compound according to claim 12, wherein R is alkyl of 1–6 carbon atoms substituted by phenyl, monoalkylamino of 1–3 carbon atoms or dialkylamino of 1–3 carbon atoms in each alkyl group.

14. A compound according to claim 4, wherein X is sulfur and R is hydrogen.

15. The compound according to claim 1, which is 2,11-dihydro-3H-s-triazolo[3,4-b][3]benzazepin-3-one.

16. The compound according to claim 1, which is 2,11-dihydro-3H-s-triazolo[3,4-b][3]benzazepine-3thione.

17. The compound according to claim 1, which is 2,11-dihydro-8,9-dimethoxy-3H-s-triazolo[3,4-b][3]benzazepin-3-one.

18. The compound according to claim 1, which is 2,11-dihydro-2-methyl-3H-s-triazolo[3,4-b][3]benzazepin-3-one.

19. The compound according to claim 1, which is 2-benzyl-2,11-dihydro-3H-s-triazolo[3,4-b][3]benzazepin-3-one.

20. The compound according to claim 1, which is 2-ethyl-2,11-dihydro-3H-s-triazolo[3,4-b][3]benzazepin-3-one.

21. The compound according to claim 1, which is 2,5,6,11-tetrahydro-2-methyl-3H-s-triazolo[3,4-b][3]benzazepin-3-one.

22. The compound according to claim 1, which is 10-chloro-2,11-dihydro-2-methyl-3H-s-triazolo[3,4-b][3]benzazepin-3-one.

23. The compound according to claim 1, which is 2,11-dihydro-2,8,9-trimethyl-3H-s-triazolo[3,4-b][3]benzazepin-3-one.

24. The compound according to claim 1, which is 2-(2-dimethylaminoethyl)-2,11-dihydro-3H-s-triazolo[3,4-b][3]benzazepin-3-one oxalate.

25. The compound according to claim 1, which is 2,11-dihydro-8,9-dimethoxy-2-methyl-3H-s-triazolo[3,4-b][3]benzazepin-3-one.

26. The compound according to claim 1, which is 2-ethyl-2,5,6,11-tetrahydro-3H-s-triazolo[3,4-b][3]benzazepin-3-one.

27. The compound according to claim 1, which is 2,5,6,11-tetrahydro-3H-s-triazolo[3,4-b][3]benzazepin-3-one.

28. The compound according to claim 1, which is 2,5,6,11-tetrahydro-8,9-dimethyl-3H-s-triazolo[3,4-b][3]benzazepin-3-one.

29. The compound according to claim 1, which is 2,5,6,11-tetrahydro-8,9-dimethoxy-3H-s-triazolo[3,4-b][3]benzazepin-3-one.

30. The compound according to claim 1, which is 2,11-dihydro-8,9-dimethyl-3H-s-triazolo[3,4-b][3]benzazepin-3-one.

31. The compound according to claim 1, which is 10-chloro-2,11-dihydro-3H-s-triazolo[3,4-b][3]benzazepin-3-one.

32. The compound according to claim 1, which is 7-chloro-2,11-dihydro-3H-s-triazolo[3,4-b][3]benzazepin-3-one.

* * * * *